United States Patent [19]

Ikuno

[11] 4,338,940
[45] Jul. 13, 1982

[54] APPARATUS FOR SUPPLYING POWER TO AN ELECTROSURGICAL DEVICE

[75] Inventor: Yuji Ikuno, Ome, Japan

[73] Assignee: Olympus Optical Co., Ltd., Tokyo, Japan

[21] Appl. No.: 177,922

[22] Filed: Aug. 13, 1980

[30] Foreign Application Priority Data

Sep. 3, 1979 [JP] Japan .................... 54-112637

[51] Int. Cl.³ ............................................. A61B 17/39
[52] U.S. Cl. ............................. 128/303.14; 128/303.17
[58] Field of Search ................. 128/303.13, 303.14, 128/303.17, 303.18, 420 R, 420 A, 421, 422, 423 R

[56] References Cited

U.S. PATENT DOCUMENTS

| | | | |
|---|---|---|---|
| 3,478,744 | 11/1969 | Leiter | 128/303.14 |
| 3,812,858 | 5/1974 | Oringer | 128/303.14 |
| 3,885,569 | 5/1972 | Judson | 128/303.14 |
| 3,898,991 | 8/1975 | Ikuno et al. | 128/303.14 |
| 4,038,984 | 8/1977 | Sittner | 128/303.14 |
| 4,051,855 | 10/1977 | Schneiderman | 128/303.14 |
| 4,281,373 | 7/1981 | Mabille | 128/303.14 X |

FOREIGN PATENT DOCUMENTS

| | | |
|---|---|---|
| 510954 | 9/1971 | Fed. Rep. of Germany . |
| 2250574 | 9/1977 | Fed. Rep. of Germany ................. 128/303.14 |

Primary Examiner—Lee S. Cohen
Attorney, Agent, or Firm—Frishauf, Holtz, Goodman & Woodward

[57] ABSTRACT

An apparatus for supplying power to an electrosurgical device comprising a power output device for providing a surgical current, a switch for supplying the power output device with a power signal to provide the surgical current, a first signal generator for supplying the switch with a switch signal to turn on and off the switch with a given timing, a second signal generator for supplying the power output device with a surgical signal having a period corresponding to the surgical current, a timer triggered by the switch signal and producing a timer signal for a given time after being triggered, and a gate for allowing the surgical current to be delivered from the power output device only while the timer signal is being produced. The surgical current is supplied from the power output device to the electrosurgical device in accordance with the logical AND of the switch signal, the timer signal and the surgical signal.

4 Claims, 17 Drawing Figures

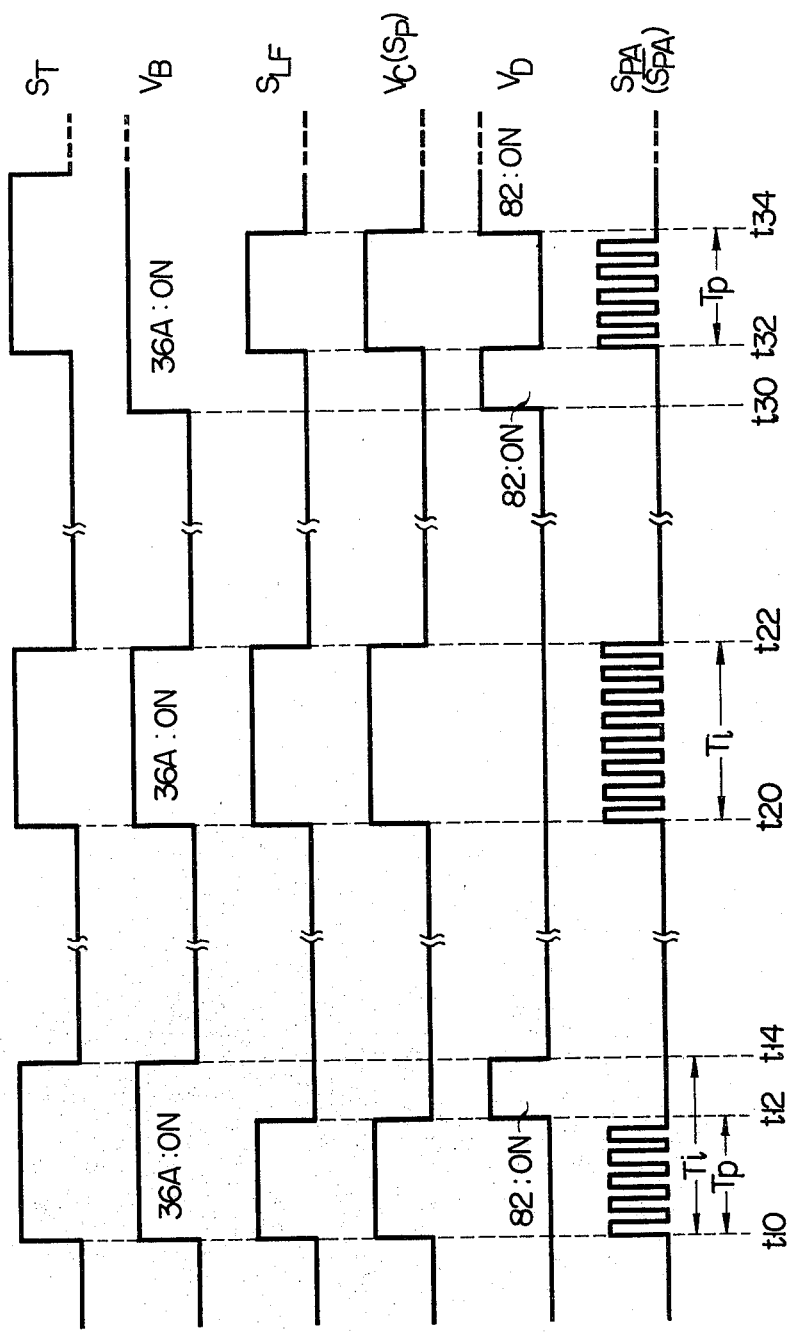

APPARATUS FOR SUPPLYING POWER TO AN ELECTROSURGICAL DEVICE

BACKGROUND OF THE INVENTION

This invention relates to a power supply apparatus used for an electrosurgical device such as an electric scalpel.

With an electric scalpel, a local high-frequency current is caused to flow through the tissue of a living body, such as a human body, and incision and stanching are conducted by utilizing Joule heat given to the tissue by the local current. Such an electric scalpel is provided with a plate electrode forming one pole of a high-frequency current path and a therapeutic electrode forming the other pole of the current path to supply the local current. The therapeutic electrode is in the form of a needle or sword having quite a narrow contact area, and the local current, i.e. a surgical current, is concentrated in close vicinity to the tissue of a living body touched by the therapeutic electrode. A small explosion of gas is caused within the tissue by the Joule heat produced during such concentration of the current, and a portion of the tissue surrounding the therapeutic electrode is incised or resected. Since protein on the incised or resected surface can be thermally coagulated, lymphatic vessels and capillaries can be blocked up for hemostasis.

Usually, a coagulation current or surgical current for the aforesaid hemostasis or stanching is obtained by switching on and off the power circuit for a power amplifier in the power supply apparatus. A semiconductor switch circuit or the like is used for switching on and off the power circuit. However, if the switch circuit breaks down to be rendered ever-on, then a continuous great current will be caused to flow through the therapeutic electrode of the electric scalpel. If such breakdown of the switch circuit occurs in stanching, a great enough amount of energy to incise the tissue will be discharged to the vicinity of the therapeutic electrode, possibly resulting in unexpected incision. Such disagreeable situation can be avoided if an element forming the switch circuit, e.g. a transistor switch, is absolutely unbreakable. When intermittently conducting great current, however, semiconductor elements are liable to deteriorate, and the most reliable ones may suddenly be broken during use.

SUMMARY OF THE INVENTION

This invention is contrived in consideration of the aforementioned circumstances, and is intended to provide an apparatus for supplying power to an electrosurgical device, capable of automatically limiting the energy of surgical current delivered from the electrosurgical device to a level with which the tissues of living bodies will never be incised even though a switch circuit formed of a semiconductor, etc. is broken to be rendered always on.

In order to attain the above object, a power supply apparatus according to this invention is so constructed that the surgical current may be supplied on the basis of the logical AND of a power signal or switch signal used for providing the surgical current, a timer signal produced for a given time, and a surgical signal corresponding to the surgical current. With such construction, even if the logic level of the power signal becomes always-"1", the logic level of the timer signal will be "1" only for a given time, so that the surgical current will be allowed to flow only within such given time. By presetting the given time to a proper value, if the switch element is broken down, it can be prevented from generating a sudden great current flow which will reopen stanched regions during a stanching operation using the electrosurgical device.

BRIEF DESCRIPTION OF THE DRAWINGS

FIG. 4 is a timing chart for illustrating the operation of the apparatus shown in FIG. 3.

DETAILED DESCRIPTION

Figure 1:
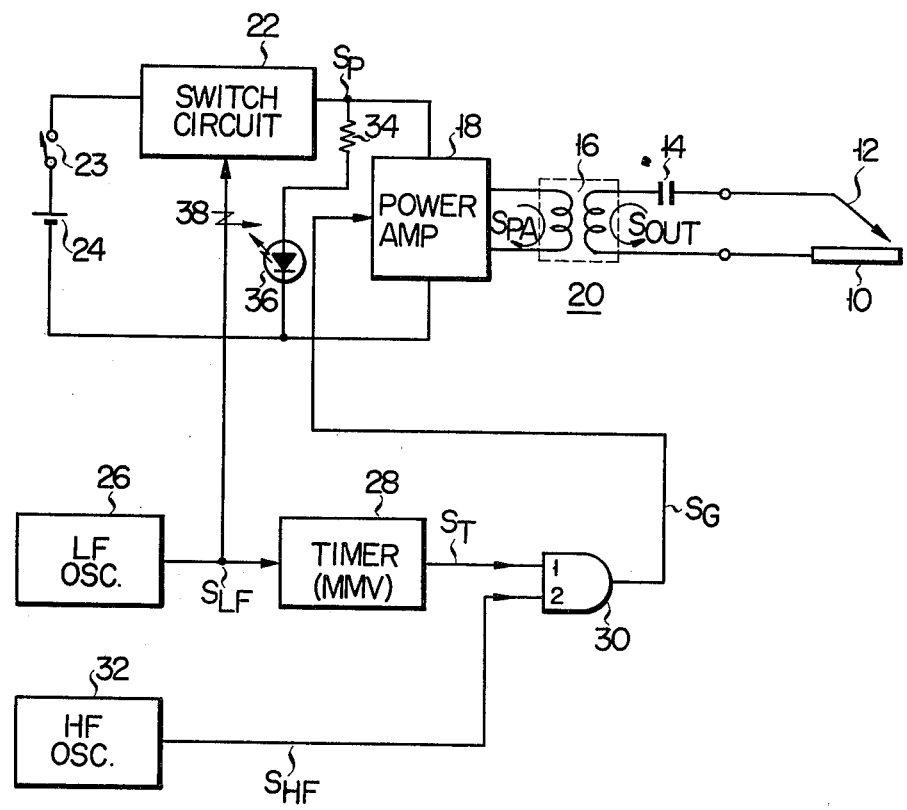
FIG. 1 is a block diagram showing the apparatus for supplying power to an electrosurgical device according to an embodiment of this invention.

Now there will be described preferred embodiments of this invention with reference to the accompanying drawings in which like or similar reference numerals are used to designate like or similar portions throughout the several views for simplicity of description.

Figure 2:
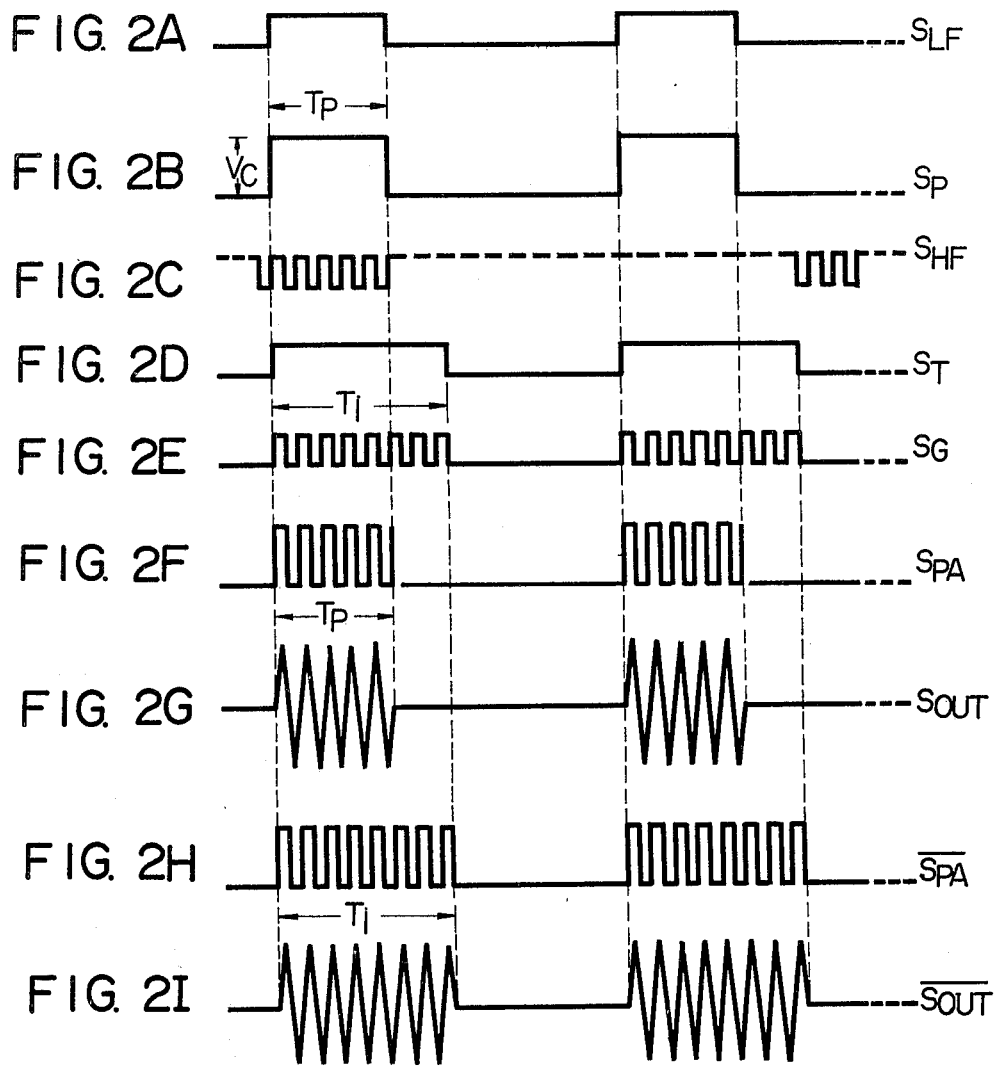
FIG. 2 is a timing chart for illustrating the operation of the apparatus shown in FIG. 1.

FIG. 1 is a block diagram for illustrating a power supply apparatus according to this invention. In FIG. 1, a plate electrode 10 and a therapeutic electrode 12 are connected to the secondary coil of an output transformer 16 through a capacitor 14. The primary coil of the output transformer 16 is coupled to a power amplifier 18. The amplifier 18, output transformer 16 and capacitor 14 constitute an output circuit (power output device or means) 20 for supplying a surgical current or coagulation current $S_{OUT}$. The amplifier 18 is coupled to a DC power source 24 through a switch circuit 22 and a power switch 23. The power source 24 may be a DC source obtained by rectifying an AC source. The switch circuit 22 is turned on and off in accordance with the logic level of a low-frequency signal (switch signal) $S_{LF}$ supplied from a low-frequency oscillator (first signal generation means) 26. The oscillator 26 can be formed of an astable multivibrator. For example, if the signal $S_{LF}$ as shown in FIG. 2A is applied to the input of the switch circuit 22, the switch circuit 22 is kept on while the logic level of the signal $S_{LF}$ is "1". Then, the switch circuit 22 supplies the amplifier 18 with a power signal $S_P$ of level $V_C$ having a pulse width of Tp as shown in FIG. 2B. The amplifier 18 is supplied with power in response to the level $V_C$ of the power signal $S_P$, and can be activated only with such level $V_C$. In other words, the amplifier 18 is activated by the logic "1" of the signal $S_{LF}$.

The signal $S_{LF}$ is applied as a trigger signal to the input of a timer circuit (timer means) 28. The timer circuit 28 is triggered at the leading edge of the signal $S_{LF}$ and produces a timer signal $S_T$ having a pulse width corresponding to a given time Ti as shown in FIG. 2D. The timer circuit 28 may, for example, be formed of a monostable multivibrator circuit. In this case, the given time Ti depends on the time constant of the multivibrator circuit.

The timer signal $S_T$ is applied to a first input terminal of an AND gate (gate means) 30. The second input terminal of the AND gate 30 is supplied with a surgical signal $S_{HF}$ as shown in FIG. 2C from a high-frequency oscillator (second signal generation means) 32. The surgical signal $S_{HF}$ is a high-frequency pulse signal having a period corresponding to the surgical current $S_{OUT}$ and a duty factor of approximately 50% at e.g. 500 kHz to 1 MHz. The AND gate 30 delivers a signal $S_G$ as shown in FIG. 2E. The signal $S_G$ is applied to the amplifier 18 as an input signal to provide the surgical current $S_{OUT}$.

As stated before, the amplifier 18 is activated only when supplied with power in response to the power signal $S_P$. Further, the amplifier 18 produces an output signal $S_{PA}$ only when the input signal $S_G$ is applied thereto. Accordingly, the signal $S_{PA}$ is delivered from the amplifier 18 when the logic levels of the signals $S_P$ and $S_G$ are both "1", as shown in FIG. 2F. The signal $S_{PA}$ may be considered to be the high-frequency signal (surgical signal) $S_{HF}$ modulated by the low-frequency signal $S_{LF}$. Under these circumstances, the amplifier 18 can be regarded as a gate circuit which, having the power signal $S_P$ as its gate signal, receives the signal $S_G$ as an input. After all, the signal $S_{PA}$ is to be obtained on the basis of the logical AND of the power signal $S_P$, timer signal $S_T$ and surgical signal $S_{HF}$ or the logical AND of the switch signal $S_{LF}$, timer signal $S_T$ and surgical signal $S_{HF}$. The signal $S_{PA}$ thus obtained is eliminated of its DC component through the output transformer 16 and capacitor 14, and is converted into the surgical current $S_{OUT}$ with signal width Tp as shown in FIG. 2G. The current $S_{OUT}$ is effectively used as a high-frequency cauterization current for coagulation of the tissues of living bodies.

In the above description, there has been mentioned a case where the arrangement of FIG. 1 operates normally. Now there will be described a case where the switch current 22 is broken from some cause. The causes of such breakdown may be classified roughly into two cases. In one case, the switch circuit 22 is left always off, while in the other case, the switch circuit 22 is left always on. In the former case, the surgical current $S_{OUT}$ completely ceases to flow, so that stanched regions will never be reopened. Also in the latter case, reopening of stanched regions can be avoided by properly selecting the given time Ti. When the switch circuit 22 is rendered always on, the logic level of the power signal $S_P$ becomes always "1". As mentioned before, however, the surgical current $S_{OUT}$ or the output signal $S_{PA}$ is given by the logical AND of the power signal, timer signal and surgical signal. Therefore, an output current $\overline{S_{PA}}$ and a surgical current $\overline{S_{OUT}}$ obtained when the switch circuit 22 is left always on have their signal duration increased from Tp to Ti, as shown in FIGS. 2H and 2I. By presetting the duration or the given time Ti to a proper value, however, the energy of surgical current delivered from the electrosurgical device can be limited to a level with which the tissues of living bodies will never be incised.

In FIG. 1, moreover, there is shown an indicator 38 formed of a resistor 34 and an LED 36 which are connected in parallel with a power circuit for the amplifier 18. The indicator 38 has a function to indicate trouble or malfunction of the switch circuit 22. When the switch circuit 22 operates normally, the LED 36 goes on and off in accordance with the period of the signal Sp. If the switch circuit 22 is rendered always on by breakdown, the LED 36 will be continuously on. If the switch circuit 22 is rendered always off by breakdown, on the other hand, the LED 36 will be left off. Thus, the failure of the switch circuit 22 can be detected through the indication state of the LED 36. The LED 36 may be replaced with a buzzer or some other alarm device.

Figure 3:
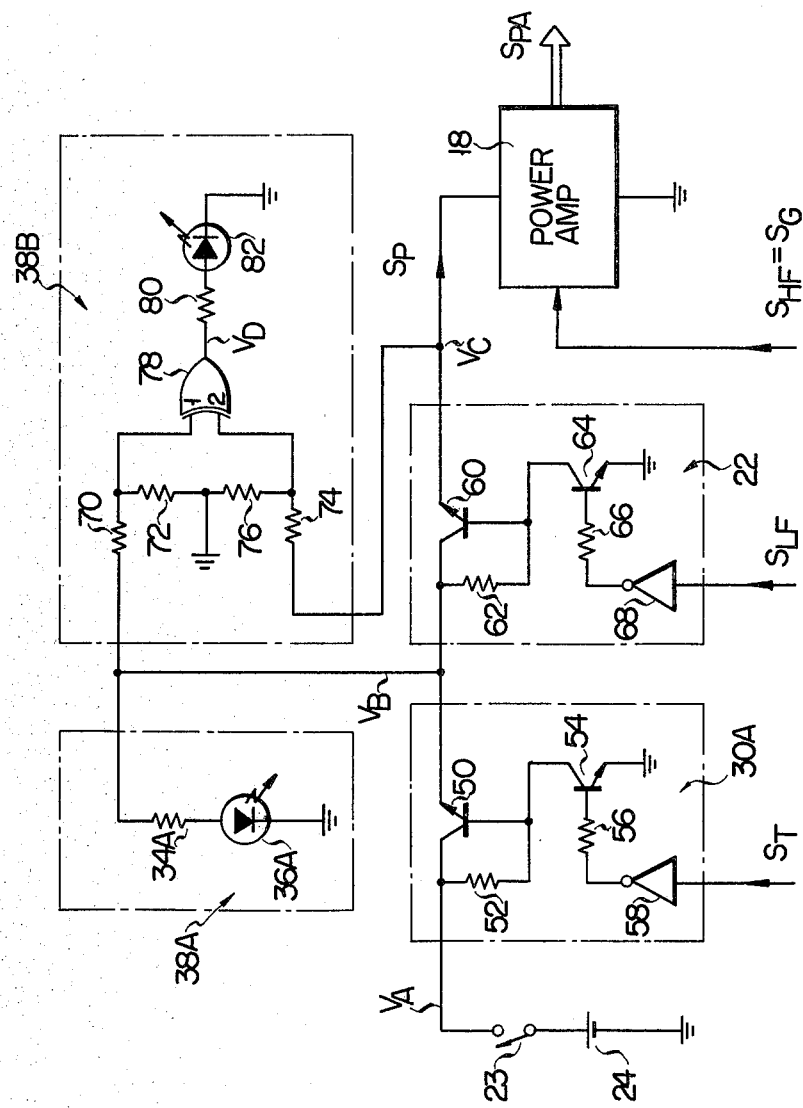
FIG. 3 shows a modification of the apparatus of FIG. 1.

FIG. 3 shows a modification of the apparatus of FIG. 1. In FIG. 1, the surgical current $S_{OUT}$ is obtained on the basis of $S_{LF}$ AND ($S_T$ AND $S_{HF}$) = $S_P$ AND $S_G$. In FIG. 3, on the other hand, the output signal $S_{PA}$, i.e. the surgical current $S_{OUT}$, is obtained on the basis of ($S_T$ AND $S_{LF}$) and $S_{HF}$ = $S_P$ AND $S_G$.

In FIG. 3, the positive pole of a DC power source 24 is connected to the collector of an NPN-type switching transistor 50 through a power switch 23. The collector of the transistor 50 is connected to the base thereof through a resistor 52. The base of the transistor 50 is grounded through the collector-emitter path of an NPN-type transistor 54. The base of the transistor 54 is connected to the output terminal of an inverter 58 through a resistor 56. The timer signal $S_T$ is applied to the input of the inverter 58. When the logic level of the signal $S_T$ is "0", the transistors 54 and 50 are turned on and off, respectively. In this case, the emitter potential $V_B$ of the transistor 50 is substantially zero. When the logic level of the signal $S_T$ becomes "1", on the other hand, the transistors 54 and 50 are turned off and on, respectively. In this case, the potential $V_B$ is a high voltage potential nearly equivalent to the collector potential $V_A$ of the transistor 50. The components 50 to 58 constitute a gate circuit (gate means) 30A to conduct or cut off the collector potential of the transistor 50 to or from the emitter side thereof in accordance with the logic level of the signal $S_T$.

The emitter of the transistor 50 is connected to the collector of an NPN-type switching transistor 60. The collector of the transistor 60 is connected to the base thereof through a resistor 62. The base of the transistor 60 is grounded through the collector-emitter path of an NPN-type transistor 64. The base of the transistor 64 is connected to the output terminal of an inverter 68 through a resistor 66. The switch signal $S_{LF}$ is applied to the input of the inverter 68. When the logic level of the signal $S_{LF}$ is "0", the transistors 64 and 60 are turned on and off, respectively. In this case, the emitter potential $V_C$ of the transistor 60, i.e. the voltage potential of the power signal $S_P$, is substantially zero. When the logic level of the signal $S_{LF}$ becomes "1", on the other hand, the transistors 64 and 60 are turned off and on, respectively. In this case, the potential $V_C$ or the signal $S_P$ is a high-voltage potential nearly equivalent to the collector potential $V_B$ of the transistor 60. The signal $S_P$ serves as a power supply signal for a power amplifier 18. The components 60 to 68 constitute a switch circuit 22 to conduct or cut off the collector potential of the transistor 60 to or from the emitter side thereof in accordance with the logic level of the signal $S_{LF}$.

With the switch 23 on, the potential $V_C$ becomes a high-voltage potential, that is, the logic level of the signal $S_P$ becomes "1" only when the logic levels of the signals $S_T$ and $S_{LF}$ are both "1". Therefore, after the logic levels of both these signals $S_T$ and $S_{LF}$ becomes "1", the amplifier 18 is activated. The surgical signal $S_{HF}$ is applied to the input of the amplifier 18. Accordingly, the output signal $S_{PA}$ is delivered from the amplifier 18 when the logic levels of all the signals $S_T$, $S_{LF}$ and $S_{HF}$ become "1". The aforementioned surgical current $S_{OUT}$ is produced when the signal $S_{PA}$ is delivered. Thus, with the arrangement of FIG. 3, the surgical current $S_{OUT}$ may be obtained on the basis of ($S_T$ AND $S_{LF}$) AND $S_{HF}$.

In FIG. 3, the transistors 50 and 60 can be broken with substantially the same probability. However, the probability that the transistors 50 and 60 will be broken at the same time is extremely low. In most cases, the transistor 60 (or 50) will be intact even if the transistor 50 (or 60) is broken; the transistor 50 (or 60) will perform a normal switching operation even though the transistor 60 (or 50) is broken. Accordingly, if the transistor 50 or 60 is damaged during the use of an electric scalpel utilizing the apparatus of FIG. 3, no great current will be caused to flow continuously through the therapeutic electrode 12 for a long time. However, if the transistor 60, for example, is broken from some cause to become ever-on, the transistor 50 may soon be broken. Therefore, if one of the transistors 50 and 60 is broken, there will be required an indicator to indicate such trouble. Accordingly, the apparatus shown in FIG. 3 is provided with first and second indicators 38A and 38B.

The emitter of the transistor 50 is grounded through a resistor 34A and an LED 36A. The components 34A and 36A constitute the first indicator 38A to notify trouble of the transistor 50, if any.

The emitter of the transistor 50 is grounded also through resistors 70 and 72, while the emitter of the transistor 60 is grounded through resistors 74 and 76. The junction point of the resistors 70 and 72 is connected to a first input terminal of an EXOR gate 78, and the junction point of the resistors 74 and 76 is connected to a second input terminal of the gate 78. The resistors 70 to 76 constitute attenuators for preventing the input circuit of the gate 78 from being broken by the voltage potential $V_B$ or $V_C$. The output terminal of the gate 78 is grounded through a resistor 80 and an LED 82. When the output potential $V_D$ of the gate 78 becomes a high-voltage potential, the LED 82 is lighted. The components 70 to 82 constitute the second indicator 38B to notify trouble of the transistor 60, if any.

FIGS. 4A to 4F are timing charts for illustrating the operation of the apparatus shown in FIG. 3. During a period t10 to t14, both the transistors 50 and 60 perform normal switching operation. Between times t10 and t14, as shown in FIGS. 4A and 4B, the LED 36A glows in response to the logic "1" of the signal $S_T$. Namely, the LED 36A is turned on and off with the same period as the oscillation period of the oscillator 26 of FIG. 1. Between times t12 and t14, as shown in FIGS. 4B and 4D, the logical levels of the two inputs of the EXOR gate 78 are different from each other. Accordingly, as shown in FIG. 4E, the LED 82 is turned on and off with the same period as the signal $S_T$ but with shorter lighting duration (equivalent to Ti-Tp). The lighting duration of the LED 82 may be extended by providing between the gate 78 and the resistor 80 a monostable multivibrator (not shown) having a given time constant and triggered by the rising edge of the output $V_D$.

During a period t20 to t22, the transistor 60 is broken to bring its collector-emitter path into conduction. In this case, the logical levels of the two inputs of the EXOR gate 78 are the same, as shown in FIGS. 4B and 4D, so that the LED 82 does not go on and off. As for the LED 36A, it goes on and off in the same manner as it does before the breakdown of the transistor 60. Therefore, if the LED 82 never goes on and off although the LED 36A does, then the transistor 60 can be considered to have been rendered always on. In such case, the switch 23 is turned off, and the transistor 60 is replaced with a new intact one.

On and after time t30, the transistor 50 is broken to bring its collector-emitter path into conduction. In this case, the LED 36A glows continuously and does not go on and off, as shown in FIG. 4B. As indicated by a period t32 to t34 in FIGS. 4E and 4F, the LED 82 goes on and off so that it may be off while the output signal $S_{PA}$ (or the surgical current $S_{OUT}$) is being produced. When the LED 36A is continuously on, the transistor 50 can be considered to have been rendered always on. In such case, the switch 23 is turned off, and the transistor 50 is replaced with a new intact one.

As described above, when the transistor 60 operates normally with the transistor 50 always on, the duration of time Tp when the signal $S_{PA}$ or the current $S_{OUT}$ is produced is the same as it is before the breakdown of the transistor 50, as shown in FIG. 4F. Accordingly, unexpected great energy will never be discharged from the therapeutic electrode 12. When the transistor 50 operates normally with the transistor 60 ever-on, on the other hand, the duration of time when the signal $S_{PA}$ is produced is extended from Tp to Ti, as shown in FIG. 4F. As already mentioned with reference to FIGS. 1 and 2, however, the time duration Ti is limited to such degree that the energy delivered from the electrosurgical device may not incise the tissue of a living body.

If the LED 36A is continuously on and the LED 82 never goes on and off at a point of time when the switch 23 is turned on, the transistors 50 and 60 can be considered to have been both rendered always on. In such case, the electrosurgical device is prohibited from use, and both these transistors 50 and 60 are replaced with new intact ones. If the defective transistor 50 or 60 is replaced with an intact one when the trouble of such transistor is detected, the aforesaid situation will hardly be brought about. If the LED 36A does not go on and off, the transistor 50 may probably have been rendered always off. If the LED's 36A and 82 go on and off in quite the same manner, it is very likely that the transistor 60 has been rendered always off. In case of such trouble that the transistor 50 or 60 is rendered always off, however, the use of the electrosurgical device may have to be prohibited, but the aforementioned unexpected incision will never be caused.

Although specific constructions have been illustrated and described herein, it is not intended that the invention be limited to the elements and constructions disclosed. One skilled in the art will recognize that other particular elements or subconstructions may be used without departing from the scope and spirit of the invention. For example, the switch circuit 22 is not limited to a transistor switch or thyristor, and the invention can be applied to any switch circuits that can be rendered always on by breakdown. Further, the specific arrangement to provide the logical AND of the power, timer, and surgical signals may vary from the ones shown in FIGS. 1 and 3. Additionally, in the arrangement of FIG. 1 or 3, a power supply apparatus to enable incision of the tissues of living bodies can be obtained by setting the signal widths Tp and Ti of the power signal $S_P$ and the timer signal $S_T$ at values great enough, that is, by lowering the oscillation frequency of the oscillator 26 and increasing the time constant of the MMV 28.

What is claimed is:

1. Apparatus for supplying surgical current to an electrosurgical device, comprising:
   power output means for providing a surgical current to an electrosurgical device;
   a source of power;
   switch means coupled to said power output means and to said power source for supplying said power output means with a power signal to provide said surgical current;

first signal generation means coupled to said switch means for supplying said switch means with a switch signal to turn on and off said switch means with given timing;

second signal generation means coupled to said power output means for supplying said power output means with a surgical signal having a period corresponding to said surgical current;

timer means triggered by said switch signal and producing a timer signal for a given period of time after being triggered, said given period of time having a predetermined value which is such that energy delivered from the electrosurgical device may not incise the tissue of a living body; and gate means coupled to said second signal generation means and to said timer means for allowing said surgical current to be delivered from said power output means to said electrosurgical device only for said given period of time while said timer signal is being produced;

whereby said surgical current is supplied from said power output means to said electrosurgical device in accordance with the logical AND of said switch signal, said timer signal and said surgical signal.

2. Apparatus according to claim 1, further comprising indication means supplied with said power signal for indicating malfunction of said switch means when said switch means is rendered always-on by said malfunction.

3. Apparatus according to claim 1 or 2, wherein said timer means produces said timer signal for a longer period of time than the time duration of said power signal produced by said switch means.

4. Apparatus according to claim 1 or 2, wherein said timer means produces said timer signal with a time duration which is longer than the time duration of said power signal produced by said switch means, and said switch means produces said power signal with a time duration which is longer than the period of said surgical signal.

* * * * *